United States Patent [19]

Matsumoto et al.

[11] Patent Number: 4,495,202

[45] Date of Patent: Jan. 22, 1985

[54] TERPHENYL DERIVATIVES AND PHARMACEUTICAL USES THEREOF

[75] Inventors: Ken Matsumoto; John S. Ward, both of Indianapolis, Ind.

[73] Assignee: Eli Lilly and Company, Indianapolis, Ind.

[21] Appl. No.: 506,931

[22] Filed: Jun. 22, 1983

[51] Int. Cl.$^3$ .................... A61K 31/09; C07C 43/205; C07C 43/225

[52] U.S. Cl. .................... 514/721; 568/643; 514/825

[58] Field of Search .................... 568/643; 424/341

[56] References Cited

U.S. PATENT DOCUMENTS

| | | | |
|---|---|---|---|
| 4,153,703 | 5/1979 | Harrison | 424/270 |
| 4,168,315 | 9/1979 | Rynbrandt et al. | 424/270 |
| 4,197,306 | 4/1980 | Harrison | 424/270 |
| 4,322,428 | 3/1982 | Matsumoto et al. | 424/270 |
| 4,330,552 | 5/1982 | Cherkofsky | 424/273 R |

FOREIGN PATENT DOCUMENTS 5219 11/1979 European Pat. Off. .

OTHER PUBLICATIONS

*J. Heterocyclic Chem.,* 19, 1165, (1982).
*Journal of Medicinal Chemistry,* 24, 1507, (1981).
Derwent E/40 84068, abstracting European Patent Application, 61,425.

*Primary Examiner*—Bernard Helfin
*Attorney, Agent, or Firm*—Charles W. Ashbrook; Arthur R. Whale

[57] ABSTRACT

This invention provides for certain novel terphenyl derivatives, their pharmaceutical formulations, and a method of treating pain, fever, thrombosis, inflammation, and arthritis.

20 Claims, No Drawings

TERPHENYL DERIVATIVES AND PHARMACEUTICAL USES THEREOF

BACKGROUND OF THE INVENTION

It is an object of this invention to provide novel 4'-substituted-4,4''-dimethoxy-1,1':2',1''-terphenyl derivatives. These compounds are active as prostaglandin synthetase inhibitors, analgesic agents, anti-inflammatory agents, anti-arthritic agents, antipyretic agents, and antithrombotic agents.

SUMMARY OF THE INVENTION

This invention provides for compounds of the Formula I

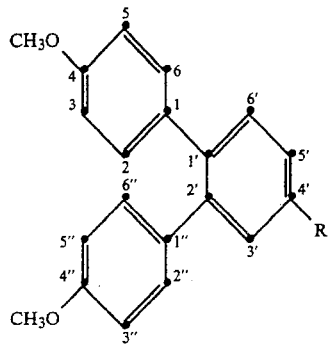

I wherein R is trifluoromethyl, phenyl, or phenyl substituted with iodo, bromo, chloro, fluoro or trifluoromethyl.

Further provided by this invention are pharmaceutical formulations for these compounds and a method for treating pain, fever, thrombosis, inflammation, and arthritis in mammals using compounds of Formula I or their pharmaceutical formulations.

DETAILED DESCRIPTION AND PREFERRED EMBODIMENT

The present invention relates to new organic compounds that are useful in the treatment of pain, fever, thrombosis, inflammation, and arthritis in mammals. The compounds of Formula I are chemically known as 4'-substituted-4,4''-dimethoxy-1,1':2',1''-terphenyls. A preferred group of compounds are the compounds of Formula I wherein R is trifluoromethyl or phenyl substituted with bromo, chloro, or fluoro. Especially preferred compounds are those wherein the halo substituents are substituted at the 4-position of the phenyl ring.

Some of the compounds of this invention can be prepared by the following reaction scheme:

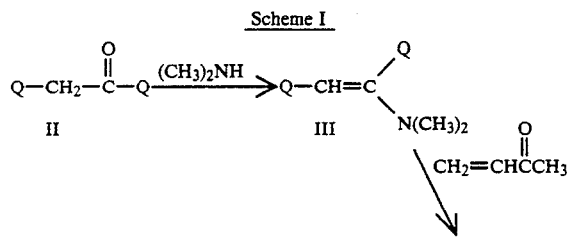

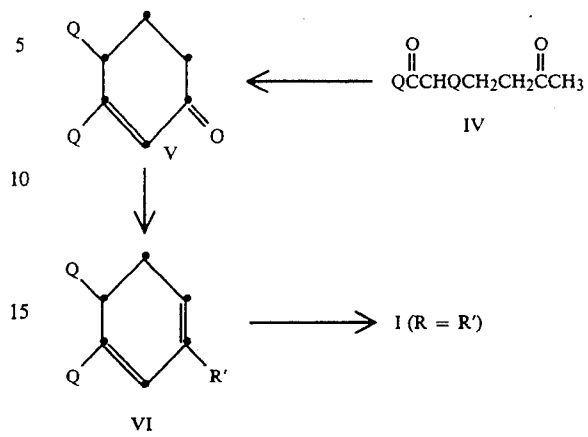

wherein Q is 4-methoxyphenyl and R' is phenyl or phenyl substituted with iodo, bromo, chloro, fluoro, or trifluoromethyl.

According to Scheme I, desoxyanisoin II is treated with dimethylamine or any other suitable secondary amine to provide the corresponding enamine III. The transformation to the enamine is preferably carried out in a non-reactive solvent, such as diethyl ether or toluene, in the presence of a Lewis acid such as titanium tetrachloride, at temperatures from about −20° C. to about 30° C. A Michael reaction is performed with the enamine on methyl vinyl ketone to provide the corresponding diketone IV. This reaction is best accomplished simply by heating the two compounds in a non-reactive solvent, such as acetonitrile, preferably at the reflux temperature of the solution. The diketone can then be cyclized to the substituted 2-cyclohexenone V by heating in the presence of an acid such as phosphoric acid or a base such as potassium hydroxide in a non-reactive solvent, such as water/alcohol, under the typical aldol condensation conditions, preferably at the reflux temperature of the reaction mixture. The cyclohexenone derivative can then be treated with the lithium or magnesium salt of the appropriate benzene derivative at temperatures of 0° C. to −78° C. in a low-melting non-reactive solvent such as tetrahydrofuran, to provide the intermediate 2-cyclohexen-1-ol derivative which, after heating with an acid, such as p-toluenesulfonic acid, in a solvent such as benzene or toluene at temperatures from about 30° C. up to the reflux temperature of the solution, provides the cyclohexadiene derivative VI. This intermediate is then heated with a dehydrogenation reagent such as palladium-on-carbon, manganese dioxide, chloranil, or especially DDQ in a solvent such as benzene or toluene at temperatures of about 30° C. up to the reflux temperature of the solution to provide the desired triaryl benzene derivative of this invention (I, R=R').

The trifluoromethyl derivative of this invention (I, R is —CF$_3$) is prepared according to Scheme II:

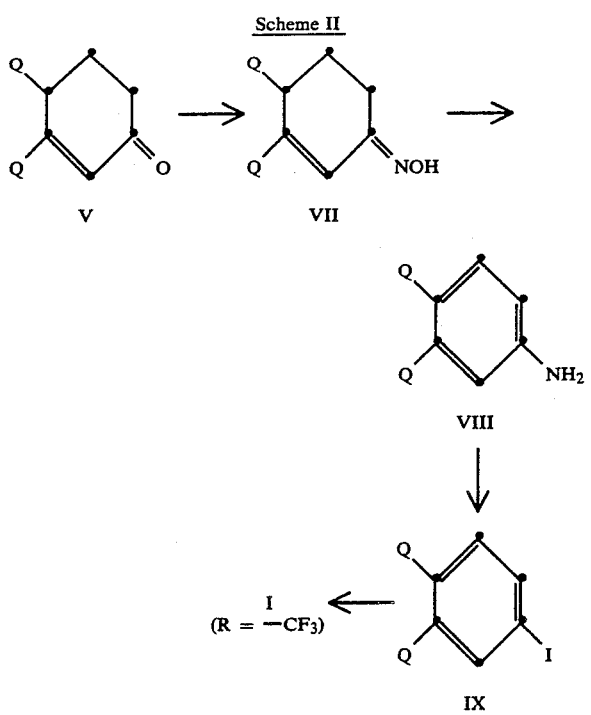

where Q is 4-methoxyphenyl.

The 2-cyclohexenone derivative V prepared in Scheme I is heated with hydroxylamine in a non-reactive solvent such as an alcohol to provide the corresponding oxime derivative VII. Heating the oxime with acetic acid, acetic anhydride, and hydrogen chloride provides the desired N-acetylated aniline derivative which is transformed into the corresponding aniline intermediate VIII upon basic hydrolysis. The aniline is transformed to the corresponding iodo intermediate IX via the Sandmeyer reaction. This aryl iodide is then transformed into the desired trifluoromethyl compound of this invention on heating with bis(trifluoromethyl)mercury, copper, and N-methyl-2-pyrrolidinone.

The compounds of this invention wherein R is trifluoromethyl-substituted phenyl can also be prepared from the corresponding iodophenyl derivatives following the same bis(trifluoromethyl)mercury/copper procedure described above.

The starting materials and reagents required for the preparation of the compounds of Formula I are either commercially available, are known in the art, or can be prepared by methods known in the art.

The compounds of this invention may be administered by various routes including the oral, rectal, transdermal, subcutaneous, intravenous, intramuscular, or intranasal routes, being usually employed in the form of a pharmaceutical composition, although it is a special feature of these compounds that they are effective following oral administration. Such compositions are prepared in a manner well known in the pharmaceutical art and comprise at least one active compound. Accordingly, the invention includes a pharmaceutical composition comprising as active ingredient a compound of Formula I associated with a pharmaceutically acceptable carrier.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propyl-hydroxybenzoates, talc, magnesium stearate or mineral oil. The formulations can additionally include lubricating agents, wetting agents, emulsifying and suspending agents, preserving agents, sweetening agents or flavoring agents. The compositions of the invention may, as is well known in the art, be formulated so as to provide quick, sustained or delayed release of the active ingredient after administration to the patient.

The oral absorption of the novel compounds of this invention in mammals is greatly enhanced by administering the compounds of Formula I in a lipid-containing vehicle. Lipid vehicles include oils, oil emulsions, sterol esters, waxes, vitamin A esters, vegetable oils such as corn oil, coconut oil, and safflower oil, animal fats such as lard and spermaceti, phospholipids, and synthetic triglycerides such as Medium Chain Triglycerides (MCT-$C_8$-$C_{10}$ chain) and Long Chain Triglycerides (LCT-$C_{16}$-$C_{18}$ chain).

Excipients can also be added and include glycols, such as polyethylene glycol and polypropylene glycol, cellulose, starch, and the like.

Although oil alone can be used to administer the compound, if the mammal receiving the compound-oil mixture can rapidly digest and absorb the oil, an oil emulsion is the preferred method of administration. The preferred oil emulsion is a corn oil-acacia emulsion, formed by dissolving the compound in corn oil and then emulsifying the mixture with a ten percent acacia solution.

Other emulsifiers or emulsifying agents can include natural emulsifiers, such as acacia, phospholipids such as lecithin, gelatin, and cholesterol, and synthetic emulsifiers such as glyceryl esters, like glyceryl monostearate, sorbitan fatty acid esters, like sorbitan monopalmitate (Span 40), polyoxyethylene sorbitan fatty acid esters, like polyoxyethylene sorbitan monopalmitate (Tween 40) and polyoxyethylene sorbitan monooleate (Tween 80), and polyoxyethylene glycol esters, like polyoxyethylene glycol monostearate.

Other methods of administration include fluid or solid unit dosage forms, such as capsules, slurries, suspensions, and the like. For example, one form is a hard gelatin capsule containing the compound dissolved in fat. First, the compound is dissolved in the fat, while the fat is in a liquid state, and the mixture is then solidified, resulting in a homogenous amorphous solution. The mixture is then pulverized and placed in a hard gelatin capsule. An emulsifier can also be added to the mixture, if desired.

Alternatively, fluid unit dosage forms, such as soft gelatin capsules, can be used to administer the compounds. These capsules are prepared by machine encapsulation of a slurry of the compound and an acceptable lipid vehicle. A slurry alone without encapsulation can also be administered.

Still another fluid unit dosage form is a suspension, which is prepared with a syrup vehicle aided by a suspending agent, such as acacia, tragacanth, methylcellulose, and the like.

A further method of administration is to orally administer the compound to a mammal previously fed a fatty meal, thereby using the fats consumed in the meal as the lipid-containing vehicles. Before the compound is administered to the mammal, the compound is micronized and coated with a surfactant, such as acacia.

Therefore, one preferred aspect of this invention is a pharmaceutical formulation comprising an effective amount of a compound of Formula I in combination with a pharmaceutically acceptable lipid-containing vehicle. A surfactant or emulsifier can also be added to the formulation.

Another preferred aspect of this invention is a pharmaceutical formulation comprising an effective amount of a compound of Formula I in combination with a pharmaceutically acceptable surfactant-containing vehicle. This formulation is administered with or after the mammal has a fatty meal.

Preferably the compositions are formulated in a unit dosage form, each dosage containing from about 5 to 500 mg., more usually about 25 to 300 mg., of the active ingredient. The term "unit dosage form" refers to physically discrete units suitable as unitary dosages for mammals, including human subjects, each unit containing a predetermined quantity of active material calculated to produce the desired therapeutic effect, in association with the required pharmaceutical carrier.

The active compounds are effective over a wide dosage range. For example, dosages per day will normally fall within the range of about 0.5 to 300 mg./kg. In the treatment of adult humans, the range of about 1 to 50 mg./kg., in single or divided doses, is preferred. However it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms, and therefore the above dosage ranges are not intended to limit the scope of the invention in any way.

The following preparations and examples further illustrate the preparation of the starting materials, intermediates, and compounds of this invention. The examples are illustrative only and are not intended to limit the scope of the invention in any way.

EXAMPLE 1

4'-(4-Fluorophenyl)-4,4''-dimethoxy-1,1':2',1''-terphenyl

A. Preparation of 4-methoxy-α-[(4-methoxyphenyl)methylene]-N,N-dimethylbenzenemethanamine.

A solution of 307.56 g. of desoxyanisoin in three liters of diethyl ether was cooled to about 0° C. by means of an external ice/alcohol bath. Under a nitrogen atmosphere, 441 ml. of dimethylamine were added to the solution with stirring. A solution of 79 ml. of titanium tetrachloride in 500 ml. of toluene was then added to the reaction mixture over a 90 minute period at such a rate to keep the temperature below 5° C. The reaction was then allowed to stir overnight at room temperature. The reaction was filtered and the precipitate was washed with two liters of diethyl ether. The ether filtrate and wash were combined and evaporated in vacuo. The residue was crystallized from ether/Skelly B to provide 272.2 g. of the desired title intermediate, m.p. about 67°-69° C.

B. Preparation of 1,2-bis(4-methoxyphenyl)-1,5-hexanedione

A solution of 268.77 g. of 4-methoxy-α-[(4-methoxyphenyl)methylene]-N,N-dimethylbenzenemethanamine and 231 ml. of methyl vinyl ketone in one liter of acetonitrile was heated at reflux overnight. The reaction mixture was cooled and evaporated to dryness in vacuo. The residue was poured into two liters of 4N hydrochloric acid and extracted four times each with one liter of ethyl acetate. The combined ethyl acetate layers were washed five times with water, dried over sodium sulfate, filtered and evaporated to dryness. The residue was dissolved in 2.5 liters of diethyl ether and brought to a final volume of four liters with cyclohexane. The solution was then evaporated to a volume of about 2.5 liters on a hot plate. The solution was cooled, scratched, and seeded. Filtration afforded 251.5 g. of the desired dione intermediate, m.p. about 62°-65° C.

C. Preparation of 3,4-bis(4-methoxyphenyl)-2-cyclohexen-1-one

A solution of 212.0 g. of 1,2-bis(4-methoxyphenyl)-1,5-hexanedione and 650 ml. of 2N potassium hydroxide in three liters of 2B ethanol was heated to reflux for two hours. The solution was cooled and 110 ml. of concentrated hydrochloric acid were added. The solution was then concentrated in vacuo. One liter of water and 1.5 liters of ethyl acetate were added to the residue. The layers were separated. The aqueous layer was extracted three times each with 800 ml. of ethyl acetate. The combined organic layers were washed four times with water, dried over sodium sulfate, filtered and evaporated in vacuo to provide 195.6 g. of the desired cyclohexenone intermediate as an oil.

D. Preparation of 1-[4,5-bis(4-methoxyphenyl)-1,5-cyclohexadien-1-yl]-4-fluorobenzene A solution of 6.11 ml. of 4-bromofluorobenzene in 200 ml. of tetrahydrofuran was cooled to −60° C. by means of an external cooling bath. Under a nitrogen atmosphere, 33.75 ml. of a 1.6M solution of n-butyllithium in hexane were added at such a rate as to maintain the temperature between −65° to −55° C. After the addition was complete, the reaction was stirred for about 20 minutes. A solution of 15.11 g. of 3,4-bis(4-methoxyphenyl)-2-cyclohexen-1-one in 200 ml. of tetrahydrofuran was added over a period of about one hour. The reaction was then allowed to warm to 0° C. during the next three hours. Sixty milliliters of water were then added in a dropwise fashion. The solution was added to three liters of diethyl ether and the organic solution was washed several times with water. The organic solution was dried over sodium sulfate and evaporated in vacuo to dryness. The residue was dissolved in 400 ml. of toluene and treated with 2.5 g. of p-toluenesulfonic acid.

The solution was allowed to reflux overnight. The solvent was then removed by evaporation and the residue was purified by chromatography to afford 13.98 g. of the title diene intermediate.

E. Preparation of 4'-(4-fluorophenyl)-4,4''-dimethoxy-1,1':2',1''-terphenyl.

To a solution of 13.91 g. of 1-[4,5-bis(4-methoxyphenyl)-1,5-cyclohexadien-1-yl]-4-fluorobenzene in 500 ml. of toluene were added 9.08 g. of 2,3-dichloro-5,6-dicyano-1,4-benzoquinone (DDQ). The solution was allowed to reflux under a nitrogen atmosphere for 20 hours employing a Dean-Stark trap. After cooling, the reaction mixture was filtered and the filtrate was evaporated in vacuo. The residue was purified by chromatography. The appropriate fractions were combined, evaporated, and recrystallized from diethyl ether/Skelly B to provide 6.08 g. of the desired product as a yellow solid, m.p. about 107°–110° C.

Analysis: $C_{26}H_{21}FO_2$; Calc.: C, 81.23; H, 5.51; Found: C, 80.95; H, 5.33.

EXAMPLES 2–5

Following the procedures of Examples 1D and 1E, the following compounds were prepared from the appropriate bromobenzene derivative.

2. 4'-Phenyl-4,4''-dimethoxy-1,1':2',1''-terphenyl, m.p. about 106°–108° C.

Analysis: $C_{26}H_{22}O_2$; Calc.: C, 85.22; H, 6.05; Found: C, 85.29; H, 6.09.

3. 4'-(4-Chlorophenyl)-4,4''-dimethoxy-1,1':2',1''-terphenyl, m.p. about 143°–144° C.

Analysis: $C_{26}H_{21}ClO_2$; Calc.: C, 77.90; H, 5.28; Found: C, 77.71; H, 5.11.

4. 4'-(4-Bromophenyl)-4,4''-dimethoxy-1,1':2',1''-terphenyl, m.p. about 152°–154° C.

Analysis: $C_{26}H_{21}BrO_2$; Calc.: C, 70.12; H, 4.75; Found: C, 70.38; H, 4.84.

5. 4'-(3-Fluorophenyl)-4,4''-dimethoxy-1,1':2',1''-terphenyl, m.p. about 127°–129° C.

Analysis: $C_{26}H_{21}FO_2$; Calc.: C, 81.23; H, 5.51; Found: C, 81.16; H, 5.53.

EXAMPLE 6

4'-Trifluoromethyl-4,4''-dimethoxy-1,1':2',1''-terphenyl

A. Preparation of 3,4-bis(4-methoxyphenyl)-2-cyclohexen-1-one oxime

A solution of 188.6 g. of 3,4-bis(4-methoxyphenyl)-2-cyclohexen-1-one and 84.8 g. of hydroxylamine hydrochloride in 1.5 liters of methanol was heated to reflux for three hours. The reaction was then stirred overnight at room temperature and evaporated in vacuo. To the residue were added one liter of ethyl acetate and 600 ml. of water. The layers were separated and the organic layer was washed three times each with 500 ml. of water. The organic layer was dried over sodium sulfate, filtered, and evaporated in vacuo to provide 192.59 g. of the title oxime intermediate.

B. Preparation of 4'-acetamido-4,4''-dimethoxy-1,1':2',1''-terphenyl

Hydrogen chloride gas was bubbled into a solution of 61.0 g. of 3,4-bis(4-methoxyphenyl)-2-cyclohexen-1-one oxime in 300 ml. of acetic acid and 215 ml. of acetic anhydride for about three hours. The temperature increased to about 70° C. and when the temperature began to drop, heat was applied by means of a heating mantle in order to maintain reflux. When the gas addition was stopped, heating was also stopped and the reaction mixture was stirred overnight at room temperature. The reaction was then evaporated in vacuo to provide 61.86 g. of the desired acetamido intermediate, m.p. about 142°–145° C.

C. Preparation of 4'-amino-4,4''-dimethoxy-1,1':2',1''-terphenyl

A solution of 10.0 g. of 4'-acetamido-4,4''-dimethoxy-1,1':2',1''-terphenyl in 250 ml. of 2B ethanol and 30 ml. of 5N sodium hydroxide was allowed to reflux overnight. Another 30 ml. of 5N sodium hydroxide were added and the reaction was allowed to reflux an additional 24 hours. The solution was then treated with 23 ml. of hydrochloric acid and evaporated in vacuo. The residue was taken up in 500 ml. of diethyl ether and 500 ml. of ethyl acetate. The organic solution was washed with water until neutral, dried over sodium sulfate, filtered, and evaporated in vacuo. The residue was crystallized from diethyl ether to provide 6.42 g. of the desired amino intermediate, m.p. about 115°–117° C.

D. Preparation of 4'-iodo-4,4''-dimethoxy-1,1':2',1''-terphenyl

A solution of 53.9 g. of 4'-amino-4,4''-dimethoxy-1,1':2',1''-terphenyl in 79 ml. of hydrochloric acid and 120 ml. of water was cooled by means of an external ice bath to about 0° C. A solution of 13.11 g. of sodium nitrate in 100 ml. of water was added over a ten minute period. After stirring an additional ten minutes, a solution of 29.9 g. of potassium iodide in 100 ml. of water was added over a 30 minute period. The solution was allowed to stand overnight without stirring. The reaction was then heated on a steam bath for 30 minutes. After cooling, two liters of ethyl acetate were added. The layers were separated and the aqueous layer was extracted four times each with 500 ml. of ethyl acetate. The combined organic extracts were washed four times each with 250 ml. of a 10% aqueous sodium thiosulfate solution, dried over sodium sulfate, filtered and evaporated in vacuo. The residue was purified by chromatography over silica gel to provide 35.12 g. of the desired iodo intermediate.

E. Preparation of 4'-trifluoromethyl-4,4''-dimethoxy-1,1':2',1''-terphenyl

A suspension of 135.4 g. of bis(trifluoromethyl)mercury and 101.4 g. of copper powder in 600 ml. of N-methyl-2-pyrrolidinone was heated to about 140° C. for about 140 minutes. A solution of 47.5 g. of 4'-iodo-4,4''-dimethoxy-1,1':2',1''-terphenyl in 500 ml. of N-methyl-2-pyrrolidinone was added over a 90 minute period. The reaction was then heated at about 150° C. overnight. After cooling, the reaction mixture was added to three liters of diethyl ether. The organic solution was washed four times each with 500 ml. of water, dried over sodium sulfate, filtered and evaporated in vacuo. The residue was purified by chromatography. The appropriate fractions were pooled and evaporated to dryness, and the residue was crystallized from Skelly B to provide 27.15 g. of the desired title product, m.p. about 82°-84° C.

Analysis: $C_{21}H_{17}F_3O_2$; Calc.: C, 70.38; H, 4.78; Found: C, 70.62; H, 4.50.

The following formulation examples may employ as active compounds any of the pharmaceutical compounds of this invention.

EXAMPLE 7

Hard gelatin capsules are prepared using the following ingredients:

|  | Quantity (mg./capsule) |
| --- | --- |
| Active compound | 250 |
| Starch dried | 200 |
| Magnesium stearate | 10 |

The above ingredients are mixed and filled into hard gelatin capsules in 460 mg. quantities.

EXAMPLE 8

A tablet formula is prepared using the ingredients below:

|  | Quantity (mg./tablet) |
| --- | --- |
| Active compound | 250 |
| Cellulose, microcrystalline | 400 |
| Silicon dioxide, fumed | 10 |
| Stearic acid | 5 |

The components are blended and compressed to form tablets each weighing 665 mg.

EXAMPLE 9

An aerosol solution is prepared containing the following components:

|  | Weight % |
| --- | --- |
| Active ingredient | 0.25 |
| Ethanol | 29.75 |
| Propellant 22 (Chlorodifluoromethane) | 70 |

The active compound is mixed with ethanol and the mixtuire added to a portion of the propellant 22, cooled to −30° C. and transferred to a filling device. The required amount is then fed to a stainless steel container and diluted further with the remainder of the propellant. The valve units are then fitted to the container.

EXAMPLE 10

Tablets each containing 60 mg. of active ingredient are made up as follows:

| Active ingredient | 60 mg. |
| --- | --- |
| Starch | 45 mg. |
| Microcrystalline cellulose | 35 mg. |
| Polyvinylpyrrolidone (as 10% solution in water) | 4 mg. |
| Sodium carboxymethyl starch | 4.5 mg. |
| Magnesium stearate | 0.5 mg. |
| Talc | 1 mg. |
| Total | 150 mg. |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLE 11

Capsules each containing 80 mg. of medicament are made as follows:

| Active ingredient | 80 mg. |
| --- | --- |
| Starch | 59 mg. |
| Microcrystalline cellulose | 59 mg. |
| Magnesium stearate | 2 mg. |
| Total | 200 mg. |

The active ingredient, cellulose, starch and magnesium stearate are blended, passed through a No. 45 mesh U.S. sieve, and filled into hard gelatin capsules in 200 mg. quantities.

EXAMPLE 12

Suppositories each containing 225 mg. of active ingredient are made as follows:

| Active ingredient | 225 mg. |
| --- | --- |
| Saturated fatty acid glycerides to | 2,000 mg. |

The active ingredient is passed through a No. 60 mesh U.S. sieve and suspended in the saturated fatty acid glycerides previously melted using the minimum heat necessary. The mixture is then poured into a suppository mold of nominal 2 g. capacity and allowed to cool.

EXAMPLE 13

Suspensions each containing 50 mg. of medicament per 5 ml. dose are made as follows:

| Active ingredient | 50 mg. |
| --- | --- |
| Sodium carboxymethyl cellulose | 50 mg. |
| Syrup | 1.25 ml. |
| Benzoic acid solution | 0.10 ml. |
| Flavor | q.v. |
| Color | q.v. |
| Purified water to | 5 ml. |

The medicament is passed through a No. 45 mesh U.S. sieve and mixed with the sodium carboxymethylcellulose and syrup to form a smooth paste. The benzoic acid solution, flavor and color are diluted with some of the water and added, with stirring. Sufficient water is then added to produce the required volume.

The compounds of this invention are useful as prostaglandin synthetase inhibitors, analgesic agents, anti-inflammatory agents, anti-arthritic agents, anti-pyretic agents, and antithrombotic agents. The compounds are especially useful as analgesic and anti-inflammatory agents. In addition, the compounds have been demonstrated to have a low potential for phototoxic side effects.

The analgesic activity of a number of compounds provided by this invention has been determined in the standard mouse writhing assay. Writhing, which is characterized by contraction of the abdominal musculature, extension of the hindlegs, and rotation of the trunk, was induced in Cox standard strain albino male mice. The mice, weighing 18–24 grams, were fasted overnight and given the test compound by gavage in a corn oil-acacia emulsion (5%) three hours before writhing was induced by the intraperitoneal administration of acetic acid (0.60 percent). Each treatment group consisted of five mice. The total number of writhes for the treatment group was determined during a 10-minute observation starting five minutes after acetic acid administration. Control groups had a total of 40–60 writhes per observation period. Table I which follows presents typical test results obtained with certain of the compounds of this invention. The results in the mouse writhing assay are presented as the effective oral (p.o.) dose in mg./kg. of the tested compound required to inhibit induced writhing in the test animals by fifty percent ($ED_{50}$).

TABLE I

| Compound of Example No. | Mouse Writhing $ED_{50}$ (mg./kg. p.o.) |
|---|---|
| 1 | 11.8* |
| 2 | 14.6 |
| 3 | 14.2 |
| 4 | 72.8 |
| 5 | 8.9 |
| 6 | 5.6 |

*at four hours post dosing, the $ED_{50}$ was 3.9 mg./kg. p.o.

Established adjuvant-induced arthritis test in rats

Certain compounds of this invention were tested for their ability to alter hind paw swelling and bone damage resulting from adjuvant-induced edema in rats. In order to quantitate the inhibition of hind paw swelling resulting from adjuvant-induced arthritis, two phases of inflammation have been defined: (1) the primary and secondary injected hind paw, and (2) the secondary uninjected hind paw, which generally begins developing about eleven days from the induction of inflammation in the injected paw.

One group of five rats received no treatment (normal control). Adjuvant arthritis was induced in male Lewis-Wistar rats (200–210 grams) on test day one by a single subplantar injection into the right hind paw of 0.1 ml. of a 0.5% suspension of heat-killed, lyophilized *Mycobacterium tuberculosis* (Calbiochem-Perrigen-C) in mineral oil (a modification of a method reported by Winder et al., *Arth. Rheum.*, 9, 394–397 (1966)). Only animals in which the non-injected paw measured at least a volume of 0.5 ml. greater than normal control animals on day 14 were selected for the rest of the experiment. One group of ten rats ("TB control") received no further treatment. Each compound to be tested was administered as a corn oil-acacia emulsion by gavage to rats (groups of five each) in daily oral doses, beginning on day 15 and continuing through the 29th day after the adjuvant injection (15 doses). Paw volumes were measured by mercury displacement using a Statham pressure transducer and digital voltmeter. Volumes of both the injected and the uninjected hind paws were measured on days 14, 16, 18, 21, 23, 25, 28, and 30. The paw volume measurements of the uninjected paw beginning with day 14 through day 30 were computer plotted for the TB controls, the normal controls, and the drug-treated animals, and the areas under the curves [(TB controls minus normal controls) and (drug-treated animals minus normal controls)] were determined. The results are summarized in Table II.

TABLE II

| Inhibition of Uninjected Paw Volume Inflammation Days 14 through 30 | | |
|---|---|---|
| Compound of Example No. | Dose (mg./kg. p.o. × 15) | % Inhibition* |
| 1 | 25 | 55 |
| 2 | 25 | 13 |
| 3 | 25 | 52 |
|   | 10 | 31 |
| 4 | 25 | 34 |
| 5 | 25 | 40 |
| 6 | 10 | 48 |

*% inhibition is the difference of the areas under the curves (AUC) of the mean uninjected paw volumes plotted for days 14, 16, 18, 21, 23, 25, 28, and 30 according to the following formula:

$$\% \text{ inhibition} = \left[ 1 - \frac{\text{(Drug treated AUC)} - \text{(normal control AUC)}}{\text{(TB control AUC)} - \text{(normal control AUC)}} \right] \times 100$$

We claim:
1. A compound of the formula I

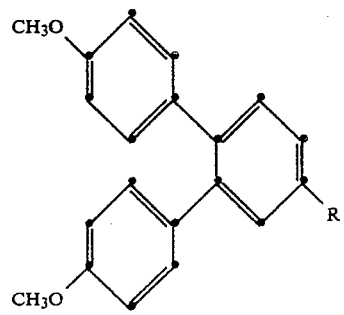

wherein R is trifluoromethyl, phenyl, or phenyl substituted with iodo, bromo, chloro, fluoro, or trifluoromethyl.

2. The compound of claim 1 which is 4'-trifluoromethyl-4,4''-dimethoxy-1,1':2',1''-terphenyl.

3. A compound of claim 1 wherein R is phenyl substituted with fluoro, chloro, or bromo.

4. A compound of claim 3 wherein the substituent is at the 4-position of the phenyl ring.

5. The compound of claim 4 which is 4'-(4-fluorophenyl)-4,4''-dimethoxy-1,1':2',1''-terphenyl.

6. The compound of claim 4 which is 4'-(4-chlorophenyl)-4,4''-dimethoxy-1,1':2',1''-terphenyl.

7. The compound of claim 4 which is 4'-(4-bromophenyl)-4,4''-dimethoxy-1,1':2',1''-terphenyl.

8. A method of treating pain, fever, thrombosis, inflammation, or arthritis which comprises administering to a mammal in need of such treatment an effective amount of a compound of claim 1.

9. The method of claim 8 in which the compound is 4'-trifluoromethyl-4,4''-dimethoxy-1,1':2',1''-terphenyl.

10. A method of claim 8 wherein R is phenyl substituted with fluoro, chloro, or bromo.

11. The method of claim 10 wherein the compound is 4'-(4-fluorophenyl)-4,4"-dimethoxy-1,1':2',1"-terphenyl.

12. A pharmaceutical formulation useful in the treatment of pain, fever, thrombosis, inflammation, or arthritis comprising an effective amount of a compound of claim 1 in association with a pharmaceutically acceptable carrier.

13. A formulation of claim 12 which contains a pharmaceutically acceptable lipid-containing vehicle.

14. A formulation of claim 13 which also contains a pharmaceutically acceptable surfactant.

15. A formulation of claim 14 wherein the lipid containing vehicle is an oil emulsion.

16. A formulation of claim 15 wherein the oil emulsion comprises corn oil and acacia.

17. The formulation of claim 16 wherein the compound is 4'-(4-fluorophenyl)-4,4"-dimethoxy-1,1':2',1"-terphenyl.

18. The formulation of claim 16 wherein the compound is 4'-(4-chlorophenyl)-4,4"-dimethoxy-1,1':2',1"-terphenyl.

19. The formulation of claim 16 wherein the compound is 4'-(4-bromophenyl)-4,4"-dimethoxy-1,1':2',1"-terphenyl.

20. The formulation of claim 16 wherein the compound is 4'-trifluoromethyl-4,4"-dimethoxy-1,1':2',1"-terphenyl.

* * * * *